(12) United States Patent
Siddiqi (10) Patent No.: US 7,956,171 B2
(45) Date of Patent: *Jun. 7, 2011

(54) NUCLEOTIDE ANALOGS (75) Inventor: Suhaib Siddiqi, Wakefield, MA (US)

(73) Assignee: Helicos Biosciences Corp., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/705,120

(22) Filed: Feb. 12, 2010

(65) Prior Publication Data

US 2010/0203541 A1    Aug. 12, 2010

Related U.S. Application Data (63) Continuation of application No. 11/804,591, filed on May 18, 2007, now Pat. No. 7,678,894.

(51) Int. Cl.
*C07H 15/00* (2006.01)
*C07H 21/02* (2006.01)
*C07H 21/04* (2006.01)
*C12P 19/34* (2006.01)
*C12Q 1/68* (2006.01)

(52) U.S. Cl. .... 536/4.1; 536/23.1; 536/24.1; 536/24.33; 536/26.6; 435/6; 435/91.1

(58) Field of Classification Search ............... 536/4.1, 536/23.1, 24.3, 24.33, 26.6; 435/6, 91.1
See application file for complete search history.

(56) References Cited

U.S. PATENT DOCUMENTS 7,678,894 B2 *  3/2010  Siddiqi ............... 536/23.1
* cited by examiner

*Primary Examiner* — Jezia Riley
(74) *Attorney, Agent, or Firm* — Thomas Meyers; Adam Schoen; Brown Rudnick LLP (57) ABSTRACT

The disclosure provides nucleotide analogs and methods of their use. Analogs of the invention comprise a reporter molecule (label) attached via the N4, N6, O4, or O6 position of the nitrogenous base portion of the analog. In a preferred embodiment, nucleotide analogs of the invention comprise a label attached to the nitrogenous base portion of the analog via a cleavable linker at the N4, O4, N6 or O6 position.

20 Claims, 1 Drawing Sheet

Figure 1

NUCLEOTIDE ANALOGS

RELATED APPLICATION

The present application is a continuation application of U.S. nonprovisional patent application Ser. No. 11/804,591, filed May 18, 2007 now U.S. Pat. No. 7,678,894, the content of which is incorporated by reference herein in its entirety.

BACKGROUND

Nucleic acid sequencing-by-synthesis has the potential to revolutionize the understanding of biological structure and function. Traditional sequencing technologies rely on amplification of sample-based nucleic acids and/or the use of electrophoretic gels in order to obtain sequence information. More recently, single molecule sequencing has been proposed as a way to obtain high-throughput sequence information that is not subject to amplification bias. See, Braslaysky, Proc. Natl. Acad. Sci. USA 100: 3960-64 (2003).

Sequencing-by-synthesis involves the template-dependent addition of nucleotides to a support-bound template/primer duplex. The added nucleotides are labeled in a manner such that their incorporation into the primer can be detected. A challenge that has arisen in single molecule sequencing involves the ability to sequence through homopolymer regions (i.e., portions of the template that contain consecutive identical nucleotides). Often the number of bases present in a homopolymer region is important from the point of view of genetic function. As most polymerases used in sequencing-by-synthesis reactions are highly-processive, they tend to add bases continuously as the polymerase traverses a homopolymer region. Most detectable labels used in sequencing reactions do not discriminate between more than two consecutive incorporations. Thus, a homopolymer region will be reported as a single, or sometimes a double, incorporation without the resolution necessary to determine the exact number of bases present in the homopolymer.

One solution to the problem of determining the number of bases present in a homopolymer is proposed in co-owned U.S. Pat. No. 7,169,560. That method involves controlling the kinetics of the incorporation reaction such that, on average, only a predetermined number of bases are incorporated in any given reaction cycle. The present invention provides an alternative solution to this problem.

SUMMARY OF THE INVENTION

Figure 1:
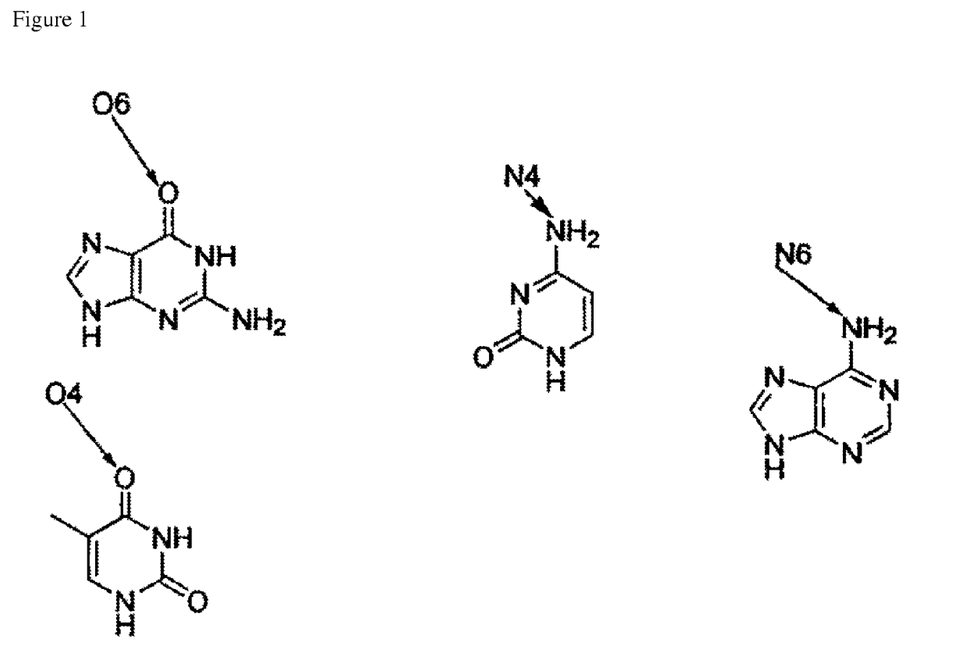
FIG. 1 shows the five common nitrogenous bases and the N6, O6, N4, and O4 positions, respectively.

The invention provides nucleotide analogs and methods of their use. Analogs of the invention comprise a reporter molecule (label) attached via the N4, N6, O4, or O6 position of the nitrogenous base portion of the analog.

In a preferred embodiment, nucleotide analogs of the invention comprise a label attached to the nitrogenous base portion of the analog via a cleavable linker at the N4, O4, N6 or O6 position. Analogs can comprise modifications at the nitrogenous base, sugar or phosphate. For example, analogs of the invention may be mono-, di-, or tri-phosphates, or may be substituted phosphates, such as difluoro, dichloro, and others. Similarly, the sugar portion of the analog may be deoxy analogs, dideoxy analogs, and may comprise a blocking moiety or other substitutions known to those of skill in the art. Additionally, substituted or altered base structures are contemplated by the invention.

In general, analogs of the invention may be placed into two broad categories. Those based upon adenine or guanine (or their analogs) have the general formula:

Wherein Y and X are independently selected from a cleavable bond, $(CH_2)n$ and $(CH_2\text{-}O\text{-}CH_2)_n$, where, in each case n is from about 1 to about 20 atoms.

Certain analogs based upon cytosine or thymine, uracil (or their analogs) have the general formula:

In each case, the nucleotide (which may be in the mono-, di-, or triphosphate form) is linked at the N4, N6, O4, or O6 position via a cleavable linker to a reporter or label. There are numerous linker structures that function in accordance with the invention to connect the nucleotide to the label. For example, the linker can be a straight-chain or branched chain alkyl, an ether, an ester, an aryl, or any combination of the foregoing. In particularly-preferred embodiments, the linker is selected from the following structures, Structure 1 and Structure 2 (where X represents the N6 or O6 position on the nucleotide; Y represents O, $(CH_2)_n$, where n=1-10, or N; and Z represents O, N, an alkyl, or an aryl group):

Structure 1

Structure 2

As the invention relates to improved structures having the linker attached at the N4, N6, O4 or O6 position, the precise structure of the linker and the label used are not of primary importance. Thus, any convenient linker can be applied at the convenience of the user.

Preferred analogs of the invention are shown below:

Structure 3

Cy-5 modification

Structure 4

Structure 3 is modified to include a label, in this case cyanine 5, as shown in Structure 4 above.

In another embodiment, an analog of the invention can take the form shown below in Structure 5:

Structure 5

X = alkyl or aryl group

In another exemplary embodiment, an O6-linked analog of the invention is presented below in Structure 6:

Structure 6

Other Exemplary structures according to the invention are shown below:

Structure 7

Structure 8

Structure 9

Structure 10

Structure 11

Structure 12

Thus, in one aspect, the invention provides a family of nucleotide analogs, each having a label attached at the N4, N6 or O4, O6 position, depending on the identity of the nitrogenous base portion as discussed above. In a preferred embodiment, the label is attached via a linker, preferably a cleavable linker, that is attached at the N4, N6 O4, or O6 position of the nitrogenous base portion of the nucleotide.

The linker can be any chemical entity that can serve to connect the base and the label. However, in a preferred embodiment, the linker is selected from alkyl or aryl groups. The linker can be from about 5 to about 100 atoms. Any cleavable linkage can be used to remove the linker and/or label from the nitrogenous base. Preferred cleavable groups include a disulfide bond, amide bond, thioamide, bond, ester bond, thioester bond, vicinal diol bond, or hemiacetal. Other cleavable bonds include enzymatically-cleavable bonds, such as peptide bonds (cleaved by peptidases), phosphate bonds (cleaved by phosphatases), nucleic acid bonds (cleaved by endonucleases), and sugar bonds (cleaved by glycosidases).

Analogs of the invention are reversible inhibitors or blockers that allow the incorporation of only one nucleotide per addition cycle in a template-dependent sequencing-by-synthesis reaction. The compositions described herein are useful in any sequencing reaction, but are especially useful in single molecule sequencing-by-synthesis reactions. Single molecule reactions are those in which the duplex to which nucleotides are added is individually optically resolvable.

The nitrogenous base portion of the nucleotide is selected from the standard Watson-Crick bases and their analogs and variants or analogs. In a specific embodiment, the invention provides a nucleotide analog comprising a nucleotide to be incorporated linked to a blocking nucleotide comprising a traditional Watson-Crick base (adenine, guanosine, cytosine, thymidine, or uridine), a sugar for example, a ribose or deoxy ribose sugar, and at least one phosphate.

The invention also provides methods for sequencing nucleic acids. In certain methods, a nucleic acid duplex, comprising a template and a primer, is positioned on a surface such that the duplex is individually optically resolvable. A sequencing-by-synthesis reaction is performed under conditions to permit addition of the labeled nucleotide analog to the primer while preventing another nucleotide or nucleotide analog from being added immediately downstream. After incorporation has been detected, inhibition is removed to permit another nucleotide to be added to the primer. Methods of the invention allow, among other things, detection and counting of consecutive nucleotides in a template homopolymer region.

DETAILED DESCRIPTION OF THE INVENTION

The invention provides nucleotide analogs that useful in sequencing-by-synthesis reactions. Analogs of the invention comprise a linker from the N6 or O6 position on the base portion of the nucleotide to a label, a blocker, or both. Thus, in one embodiment, an analog of the invention comprises a blocking group, which may be the label itself, attached via a linker or tether to the N6 or O6 position of the base, depending upon the identity of the base as described above. Blocking groups attached to analogs of the invention allow sequencing-by-synthesis reactions to occur such that only one nucleotide addition is made before subsequent additions are made to the template. This allows for sequencing through homopolymer regions (regions of the template having repeats of the same nucleotide) one base at a time which, in turn, enables counting the number of nucleotides in a homopolymer.

Analogs of the invention are based upon any of the standard Watson-Crick nucleotides or their variants, and may be in the mono-, di-, tri-, or bis phosphate configuration. The analogs can contain traditional ribose or deoxyribose sugar groups or non-traditional groups such as an acyNTP construct and others known to those skilled in the art. Analogs of the invention comprise an N4, N6 or O4, O6-linked blocker or label to enable detection of the analog upon incorporation in a sequencing-by-synthesis reaction.

As discussed above, the invention provides improved methods for sequencing a nucleic acid containing a homopolymer region. The method comprises exposing a nucleic acid template/primer duplex to (i) a polymerase which catalyzes nucleotide addition to the primer, and (ii) a labeled nucleotide triphosphate analog comprising a first nucleotide or a first nucleotide analog covalently bonded through a tether to an inhibitor under conditions that permit the polymerase to add the labeled nucleotide triphosphate analog to the primer at a position complementary to the first base in the template while preventing another nucleotide or nucleotide analog from being added to the primer at a position complementary to the next downstream base. After the exposing step, the nucleotide triphosphate analog incorporated into the primer is detected. The inhibitor is removed to permit other nucleotides to be incorporated into the primer. It is contemplated that the label, for example, one of the optically detectable labels described herein, can be removed at the same time as the inhibitor. Any of the tethered nucleotide analogs described herein can be used in this type of sequencing protocol.

The following sections discuss general considerations for nucleic acid sequencing, for example, template considerations, polymerases useful in sequencing-by-synthesis, choice of surfaces, reaction conditions, signal detection and analysis.

Exemplary Synthesis

The following synthetic pathway was used to produce a compound of the invention:

Nucleic Acid Templates

Nucleic acid templates include deoxyribonucleic acid (DNA) and/or ribonucleic acid (RNA). Nucleic acid templates can be synthetic or derived from naturally occurring sources. In one embodiment, nucleic acid template molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. Biological samples for use in the present invention include viral particles or preparations. Nucleic acid template molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid template molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA.

Nucleic acid obtained from biological samples typically is fragmented to produce suitable fragments for analysis. In one embodiment, nucleic acid from a biological sample is fragmented by sonication. Nucleic acid template molecules can be obtained as described in U.S. Patent Application Publication Number US2002/0190663 A1, published Oct. 9, 2003. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Generally, individual nucleic acid template molecules can be from about 5 bases to about 20 kb. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In a preferred embodiment, the concentration of the detergent is between 0.1% to about 2%. The detergent, particularly a mild one that is nondenaturing, can act to solubilize the sample. Detergents may be ionic or non-ionic. Examples of nonionic detergents include triton, such as the Triton® X series (Triton® X-100 t-Oct-$C_6H_4$—($OCH_2$—$CH_2$), OH, x=9-10, Triton® X-100R, Triton® X-114 x=7-8), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14E06), octyl-beta-thioglucopyranoside (octyl thiogluco-side, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulf-onate. It is contemplated also that urea may be added with or without another detergent or surfactant;

Lysis or homogenization solutions may further contain other agents, such as reducing agents. Examples of such reducing agents include dithiothreitol (DTT), 0-mercaptoethanol, DTE, GSH, cysteine, cysteamine, tricarboxyethyl phosphine (TCEP), or salts of sulfurous acid.

Nucleic Acid Polymerases

Nucleic acid polymerases generally useful in the invention include DNA polymerases, RNA polymerases, reverse transcriptases, and mutant or altered forms of any of the foregoing. DNA polymerases and their properties are described in detail in, among other places, DNA Replication 2nd edition, Kornberg and Baker, W. H. Freeman, New York, N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), Pyrococcus woesei (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al., 1991, Polynucleotides Res, 19: 4193, New England Biolabs), 9° NmTM DNA polymerase (New England Biolabs), Stoffel fragment, ThermoSequenase® (Amersham Pharmacia Biotech UK), Therminator™ (New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacterioril, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO 0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UITma DNA polymerase (from thermophile *Thermotoga maritima*; Diaz and Sabino, 1998 Braz J. Med. Res, 31:1239; PE Applied Biosystems), Tgo DNA polymerase (from *thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al., 1981, J. Biol. Chem. 256:3112), and archaeal DP1I/DP2 DNA polymerase II (Cann et al., 1998, Proc. Natl. Acad. Sci. USA 95:14250).

Both mesophilic polymerases and thermophilic polymerases are contemplated. Thermophilic DNA polymerases include, but are not limited to, ThermoSequenase., 9° NmTM, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. A highly-preferred form of any polymerase is a 3' exonuclease-deficient mutant.

Reverse transcriptases useful in the invention include, but are not limited to, reverse transcriptases from HIV, HTLV-1, HTLV-II, FeLV, My, SIV, AMV, MMTV, MoMuLV and other retroviruses (see Levin, Cell 88:5-8 (1997); Verma, Biochim Biophys Acta. 473:1-38 (1977); Wu et al., CRC Crit Rev Biochem. 3:289-347 (1975)).

Surfaces

In a preferred embodiment, nucleic acid template molecules are attached to a substrate (also referred to herein as a surface) and subjected to analysis by single molecule sequencing as described herein. Nucleic acid template molecules are attached to the surface such that the template/primer duplexes are individually optically resolvable. Substrates for use in the invention can be two- or three-dimensional and can comprise a planar surface (e.g., a glass slide) or can be shaped. A substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a nucleic acid. Substrates can include planar arrays or matrices capable of having regions that include populations of template nucleic acids or primers. Examples include nucleoside-derivatized CPG and polystyrene slides; derivatized magnetic slides; polystyrene grafted with polyethylene glycol, and the like.

Substrates are preferably coated to allow optimum optical processing and nucleic acid attachment. Substrates for use in the invention can also be treated to reduce background. Exemplary coatings include epoxides, and derivatized epoxides (e.g., with a binding molecule, such as an oligonucleotide or streptavidin).

Various methods can be used to anchor or immobilize the nucleic acid molecule to the surface of the substrate. The immobilization can be achieved through direct or indirect bonding to the surface. The bonding can be by covalent linkage. See, Joos et al., Analytical Biochemistry 247:96-101, 1997; Oroskar et al., *Clin. Chem.* 42:1547-1555, 1996; and Khandjian, *Mol. Bio. Rep.* 11:107-115, 1986. A preferred attachment is direct amine bonding of a terminal nucleotide of the template or the 5' end of the primer to an epoxide integrated on the surface. The bonding also can be through non-covalent linkage. For example, biotin-streptavidin (Taylor et al., *J. Phys. D. AppL Phys.* 24:1443, 1991) and digoxigenin with anti-digoxigenin (Smith et al., Science 253:1122, 1992) are common tools for anchoring nucleic acids to surfaces and parallels. Alternatively, the attachment can be achieved by anchoring a hydrophobic chain into a lipid monolayer or bilayer. Other methods for known in the art for attaching nucleic acid molecules to substrates also can be used.

Detection

Any detection method can be used that is suitable for the type of label employed. Thus, exemplary detection methods include radioactive detection, optical absorbance detection, e.g., UV-visible absorbance detection, optical emission detection, e.g., fluorescence or chemiluminescence. For example, extended primers can be detected on a substrate by scanning all or portions of each substrate simultaneously or serially, depending on the scanning method used. For fluorescence labeling, selected regions on a substrate may be serially scanned one-by-one or row-by-row using a fluorescence microscope apparatus, such as described in Fodor (U.S. Pat. No. 5,445,934) and Mathies et al. (U.S. Pat. No. 5,091,652). Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993), such as described in Yershov et al., Proc. Natl. Acad. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc. Such detection methods are particularly useful to achieve simultaneous scanning of multiple attached template nucleic acids.

A number of approaches can be used to detect incorporation of fluorescently-labeled nucleotides into a single nucleic acid molecule. Optical setups include near-field scanning microscopy, far-field confocal microscopy, wide-field epi-illumination, light scattering, dark field microscopy, photoconversion, single and/or multiphoton excitation, spectral wavelength discrimination, fluorophor identification, evanescent wave illumination, and total internal reflection fluorescence (TIRF) microscopy. In general, certain methods involve detection of laser-activated fluorescence using a microscope equipped with a camera. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

Some embodiments of the present invention use TIRF microscopy for imaging. TIRF microscopy uses totally internally reflected excitation light and is well known in the art. See, e.g., the World Wide Web at Nikon-instruments.jp/eng/page/products/tirf.aspx. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. The optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths.

The evanescent field also can image fluorescently-labeled nucleotides upon their incorporation into the attached template/primer complex in the presence of a polymerase. Total internal reflectance fluorescence microscopy is then used to visualize the attached template/primer duplex and/or the incorporated nucleotides with single molecule resolution.

Analysis

Alignment and/or compilation of sequence results obtained from the image stacks produced as generally described above utilizes look-up tables that take into account possible sequences changes (due, e.g., to errors, mutations, etc.). Essentially, sequencing results obtained as described herein are compared to a look-up type table that contains all possible reference sequences plus 1 or 2 base errors.

I claim:

1. A nucleotide analog, the analog comprising:
   a nitrogenous base;
   a linker attached at the O4 or O6 of the nitrogenous base; and
   a moiety attached to the nitrogenous base via the linker.

2. The analog according to claim 1, wherein the linker comprises a cleavable bond.

3. The analog according to claim 1, wherein the moiety is a label.

4. The analog according to claim 3, wherein the label is a detectable label.

5. The analog according to claim 4, wherein the detectable label is an optically detectable label.

6. The analog according to claim 5, wherein the optically detectable label is a fluorescent label.

7. The analog according to claim 6, wherein the fluorescent label is selected from the group consisting of: Cy-5, Cy-3, Joe, Rox, and TAMRA.

8. The analog according to claim 1, wherein the moiety is a blocking group.

9. The analog according to claim 1, further comprising a mono-, di-, tri-, or bis-phosphate.

10. The analog according to claim 1, further comprising a ribose sugar or a deoxyribose sugar.

11. A nucleotide analog, the analog comprising:
    a nitrogenous base;
    a linker attached at the N4 or N6 of the nitrogenous base; and
    a moiety attached to the nitrogenous base via the linker, wherein the linker comprises a cleavable bond such that a native nucleotide monophosphate is regenerated upon incorporation of the analog into a nucleic acid duplex.

12. The analog according to claim 11, wherein the moiety is a label.

13. The analog according to claim 12, wherein the label is an optically detectable label.

14. The analog according to claim 13, wherein the optically detectable label is a fluorescent label.

15. The analog according to claim 14, wherein the fluorescent label is selected from the group consisting of: Cy-5, Cy-3, Joe, Rox, and TAMRA.

16. The analog according to claim 11, wherein the moiety is a blocking group.

17. The analog according to claim 11, further comprising a mono-, di-, tri-, or bis-phosphate.

18. The analog according to claim 11, further comprising a ribose sugar or a deoxyribose sugar.

19. A method for sequencing a nucleic acid, the method comprising the steps of:
   attaching directly or indirectly a nucleic acid duplex to a surface, the duplex comprising a template portion and a primer portion hybridized thereto;
   exposing the duplex to an analog of claim 1 or claim 11 in the presence of a polymerase capable of catalyzing addition of the analog to the primer portion in a template-dependent manner;
   removing unincorporated analog and polymerase;
   detecting incorporation of analog into said primer; and
   repeating the exposing, removing, and detecting steps at least once.

20. The method according to claim 19, further comprising the step of cleaving the molecule from the analog after the detecting step.

* * * * *